United States Patent [19]

Hellberg et al.

[11] Patent Number: 5,607,966
[45] Date of Patent: Mar. 4, 1997

[54] ESTERS AND AMIDES OF NON-STEROIDAL ANTI-INFLAMMATORY CARBOXYLIC ACIDS WHICH MAY BE USED AS ANTI-OXIDANTS, 5-LIPOXYGENASE INHIBITORS AND NON-STEROIDAL ANTI-INFLAMMATORY PRODRUGS

[75] Inventors: Mark R. Hellberg, Arlington; Gustav Graff, Cleburne, both of Tex.

[73] Assignee: Alcon Laboratories, Inc., Fort Worth, Tex.

[21] Appl. No.: 362,718

[22] Filed: Dec. 23, 1994

[51] Int. Cl.$^6$ .................. C07D 311/04; A01K 31/35
[52] U.S. Cl. .................. 514/458; 514/465; 514/653; 549/407; 549/438; 564/172
[58] Field of Search .................. 549/407, 438; 564/172; 514/458, 465, 653

[56] References Cited

U.S. PATENT DOCUMENTS

| | | |
|---|---|---|
| 4,374,258 | 2/1983 | Horner .................. 549/407 |
| 4,988,728 | 1/1991 | Gerson et al. .................. 514/448 |
| 5,084,575 | 1/1992 | Kreft, III et al. .................. 546/172 |

FOREIGN PATENT DOCUMENTS

| | | | |
|---|---|---|---|
| 241043-A | 10/1987 | European Pat. Off. . | |
| 279867-A | 8/1988 | European Pat. Off. . | |
| 345592-A | 12/1989 | European Pat. Off. . | |
| 380367-A | 8/1990 | European Pat. Off. . | |
| 0387771 | 9/1990 | European Pat. Off. | ...... C07D 311/72 |
| 0527458A1 | 2/1993 | European Pat. Off. | ...... C07C 233/22 |
| 0525360A2 | 2/1993 | European Pat. Off. | ...... C07C 235/34 |
| 3407507A1 | 9/1985 | Germany . | |
| 3904674-A | 8/1990 | Germany . | |
| 64-40484A2 | 10/1989 | Japan | .................. C07D 491/052 |
| WO95/29906 | 11/1995 | WIPO . | |

OTHER PUBLICATIONS

Hammond et al., "2,3–Dihydro–5–benzofuranols as Antiooxidant–Based Inhibitors of Leukotriene Biosynthesis", *J. Med. Chem.*, vol. 32, pp. 1006–1020 (1989).

Hutchinson et al., "Drug Discovery and Development through the Genetic Engineering of Antibiotic–Producing Microorganisms", *Journal of Medicinal Chemistry*, vol. 32, No. 5, pp. 907–918 (1989).

Tseng, C., et al., "Inhibition of in Vitro Prostaglandin and Leukotriene Biosyntheses by Chinnamoyl–β–phenethylamine and N–Acyidopamine Derivatives", *Chem. Pharm. Bull.*, vol. 40, No. 2, pp. 396–400 (1992).

Campbell, W.; "Lipid–Derived Autacoids"; *Goodman and Gilman's The Pharmacological Basis of Therapeutics*, Pergman Press, New York (1990) 600–617.

Gifford, H.; "The Treatment of Sympathetic Ophthalmia"; *Ophthalmoscope* 8 (1910) 257–259.

Goa and Chrisp; "Ocular Diclofenac"; *Drugs & Aging* 2(6) (1992) 473–486.

Insel, P.; "Analgesic–Antipyretics and Antiinfmammatory Agents"; *Goodman and Gilman's The Pharmacological Basis of Therapeutics*; Pergman Press, New York (1990) 638–669, 681.

"Antioxidant properties of some chemicals vs their influence on cyclooxygenase and lipoxidase activities"; *Biochemical Pharmacology* 32 (14) (1983) 2283–2286.

Bellavite, P.; "The Superoxide–Forming Enzymatic System of Phagocytes"; *Free Radical Biology & Medicine* 4 (1988) 255–261.

Duchstein and Gurka; "Activated Species of Oxygen"; *Archives of Pharmacology* 325 (1992) 129–146.

Sies and Murphy, "Role of tocopherols in the protection of biological systems against oxidative damage"; *Journal of Photochemistry and Photobiology* 8 (1991) 211–224.

Chow, C.; "Vitamin E and Oxidative Stress"; *Free Radical Biology & Medicine* 11 (1991) 215–232.

Petty, et al.; "Protective Effects of an α–tocopherol analogue against myocardial reperfusion injury in rats"; *European Journal of Pharmacology* 210 (1992) 85–90.

Bonne, et al.; "2–(2–Hydroxy–4–methylphenyl)aminothiazole Hydrochloride as a Dual Inhibitor of Cyclooxygenase/Lipoxygenzse and a Free Radical Scavenger"; *Drug Research* 39 II, Nr. 10 (1989) 1242–1245.

Nelson, P.; "Cyclooxygenase Inhibitors"; *CRC Handbook of Eicosanoids: Prostaglandins, and Related Lipids, vol. II Drugs Acting Via the Eicosanoids*; CRC Press, Boca Raton, FL (1989) 59–133.

Cohen, et al.; "Lewis Acid Mediated Nucleophilic Substitution Reactions"; *Journal of Organic Chemistry* 54 (1989) 3282–3292.

Lambda, et al.; "Spectroscopic detection of lipid peroxidation products and structural changes in a sphingomyelin model system"; *Biochimica et Biophysica Acta* 1081 (1991) 181–187.

Skoog and Beck; "Methods of Isolating Leukocytes"; *Blood* 11 (1956) 436–454.

Graff and Anderson; "1–[4–[3–[4–[BIS(4–Fluorophenyl)hydroxymethyl]–1–peperidinyl]propoxy]–3–methoxyphenyl]ethanone (AHR–5333)"; *Prostaglandins* 38 No. 4 (1989) 473–497.

Bazan. H.; "Response of Inflammatory Lipid Mediators following Corneal Injury"; *Lipid Mediators in Eye Inflammation*.

*New Trends Lipid Mediators Res. Basel* Karger vol. 5 (1990) 1–11.

Primary Examiner—Robert Gerstl
Attorney, Agent, or Firm—Michael C. Mayo; Gregg C. Brown

[57] ABSTRACT

Compounds having anti-inflammatory and anti-oxidant activity are disclosed. The compounds are useful in preventing and treating inflammatory disorders through several mechanisms. Methods of treatment employing these properties of the compounds and corresponding pharmaceutical compositions are disclosed.

33 Claims, No Drawings

ESTERS AND AMIDES OF NON-STEROIDAL ANTI-INFLAMMATORY CARBOXYLIC ACIDS WHICH MAY BE USED AS ANTI-OXIDANTS, 5-LIPOXYGENASE INHIBITORS AND NON-STEROIDAL ANTI-INFLAMMATORY PRODRUGS

BACKGROUND OF THE INVENTION

The present invention is directed to the provision of compounds having potent anti-inflammatory and anti-oxidant activity. The invention is further directed to compositions containing the compounds of the present invention for use in pharmaceutical applications. The invention is also directed to methods of using the compounds and compositions of the present invention to prevent and treat inflammatory disorders including ocular inflammation associated with ophthalmic disease and ophthalmic surgery.

Inflammation from cellular stress can cause excessive tissue damage. Numerous biochemical pathways are known to lead to inflammation. In general, the cyclooxygenase system produces prostaglandins, while the lipoxygenase system produces leukotrienes, "HETEs" and "FFPETEs". Such agents have been associated with inflammation. See generally, *Goodman and Gilman's The Pharmacological Basis of Therapeutics*, pages 600–617, Pergman Press, New York (1990). Therapies designed to inhibit the production of these types of agents are therefore of great interest.

Non-steroidal anti-inflammatory agents (NSAIA) have been used for the treatment of inflammatory disorders. The following references may be referred to for further background concerning this use of NSAIAs:

*Ophthalmoscope*, volume 8, page 257 (1910);
*Nature*, New Biology volume 231, page 232 (1971);
*FASEB Journal*, volume 1, page 89 (1987); and
*Inflammation and Mechanisms and Action of Traditional Drugs*, Vol. I Anti-inflammatory and Anti-rheumatic drugs. Boca Raton, Fla., CRC Press, (1985).

However, there are some problems associated with NSAIA treatment including delivery to the appropriate site of action and side effects (*Goodman and Gilman's The Pharmacological Basis of Therapeutics*, pages 638–669, Pergman Press, New York (1990)).

Free radical molecules also play a major role in inflammation. These unstable chemical moieties lead to the oxidation of tissue resulting in damage. Such oxidative stress and damage has been described in *Biochemical Pharmacology*, 32(14), 2283–2286 (1983) and *Free Radicals in Biology and Medicine*, 4, 225–261 (1988). Agents that act as anti-oxidants can protect against oxidative damage. Such protection has been the subject of numerous scientific publications, including the following:

*Archives of Pharmacology*, volume 325, pages 129–146 (1992);
*Journal of Photochemistry and Photobiology*, volume 8, pages 211–224 (1991);
*Free Radicals in Biology and Medicine*, volume 11, pages 215–232 (1991); and
*European Journal of Pharmacology*, volume 210, pages 85–90 (1992).

The combination of anti-oxidant activity with other pharmacologically significant activities in a single molecule is discussed in JP 64-40484 A2 and EP 387771 A2; and compounds with cyclooxygenase/5-Lipoxygenase and anti-oxidant activity are discussed in *Drug Research*, 39(11) Number 10, pages 1242–1250 (1989). However, these references do not disclose the compounds of the present invention.

The present invention is directed to the provision of new compounds that have both potent anti-inflammatory activity and potent anti-oxidant activity in a single molecule. The use of a single chemical entity with potent anti-inflammatory and potent anti-oxidant activity provides increased protection relative to the use of a compound with singular activity. The use of a single agent having both activities over a combination of two different agents provides uniform delivery of an active molecule, thereby simplifying issues of drug metabolism, toxicity and delivery.

SUMMARY OF THE INVENTION

The present invention provides new compounds having potent anti-inflammatory and anti-oxidant activity. The dual therapeutic efficacies act in a complementary manner to reduce cellular damage. Additionally, the compounds of the present invention also exhibit other anti-inflammatory activity not present in the individual agents.

The compounds of the present invention are useful as cytoprotective agents. These compounds include a non-steroidal anti-inflammatory agent (NSAIA) moiety and an anti-oxidant moiety. In order to provide effective therapy for inflammatory disorders, the present invention takes advantage of these individual efficacies. In addition, the invention improves upon these individual efficacies by providing greater drug delivery to the target tissues by means of administering a single drug having multiple therapeutic actions. Finally, the compounds of the present invention exhibit therapeutic properties which are not present in the individual moieties of the compounds. These and other advantages of the present invention will be apparent to those skilled in the art based on the following description.

The NSAIA component of the compounds provides anti-inflammatory activity. The use of these NSAIAs will provide inhibition of cyclooxygenase, an important enzyme involved in the prostaglandin/inflammation pathway. The compounds also include an anti-oxidant component. As oxidative stress has been implicated in inflammatory responses, the presence of an anti-oxidant will further help treat the target tissue.

The compounds of the present invention also exhibit properties present only in the combined molecule, not in the individual components. One such property is the inhibitory efficacy against 5-lipoxygenase, an enzyme known to be involved in inflammation.

Another advantage of the present invention is that the anti-inflammatory moiety and the anti-oxidant moiety are linked through an amide or ester bond. Since the carboxylic acid moiety of the NSAIA has been converted to an amide or ester, the resultant molecule is neutrally charged, thus increasing lipophilicity and drug delivery. Furthermore, the amides or esters, acting as pro-drugs, can move to the site of inflammation, where proteases and esterases, present as tissue constituents or released as part of the inflammatory response, will catalyze the hydrolysis of the ester or amide and release the non-steroidal anti-inflammatory agent and anti-oxidant.

The compounds of the present invention are capable of protecting against cellular damage by a wide range of insults. Since the compounds provide this protection by decreasing free radical or oxidative damage, reducing cyclooxygenase or lipoxygenase mediated inflammation, and improving site delivery, this therapy represents an improved two-pronged approach to cytoprotection.

DETAILED DESCRIPTION OF THE INVENTION

The compounds of the present invention are of the formula (I):

$$A—X—(CH_2)_n—Y—(CH_2)_m—Z \qquad (I)$$

wherein:

A is an non-steroidal anti-inflammatory agent (NSAIA);

A—X is an ester or amide linkage derived from the carboxylic acid moiety of the NSAIA, wherein X is O or NR;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is:

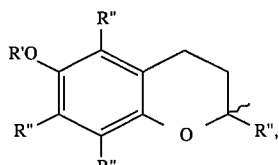

a

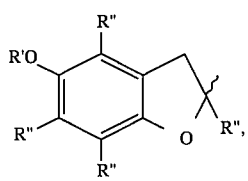

b

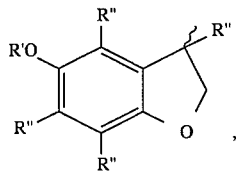

c

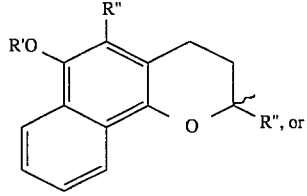

d

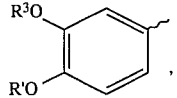

e wherein:

R' and $R^3$ are H, C(O)R, $C(O)N(R)_2$, $PO_3^-$, or $SO_3^-$;

R" is H or $C_1$–$C_6$ alkyl; and

R' and $R^3$ together may form a ring having the following structure:

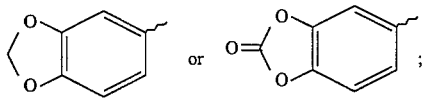

and provided that when Z is e, X is not O.

The compounds of the present invention also include pharmaceutically acceptable salts of the compounds of formula (I).

The compounds of the present invention contain a non-steroidal anti-inflammatory agent, "A", having a carboxylic moiety. A number of chemical classes of non-steroidal anti-inflammatory agents have been identified. The following text, the entire contents of which are hereby incorporated by reference in the present specification, may be referred to for various NSAIA chemical classes: *CRC Handbook of Eicosanoids: Prostaglandins, and Related Lipids, Volume II, Drugs Acting Via the Eicosanoids*, pages 59–133, CRC Press, Boca Raton, Fla. (1989). The NSAIA may be selected, therefore, from a variety of chemical classes including, but not limited to, fenamic acids, such as flufenamic acid, niflumic acid and mefenamic acid; indoles, such as indomethacin, sulindac and tolmetin; phenylalkanoic acids, such as suprofen, ketorolac, flurbiprofen and ibuprofen; and phenylacetic acids, such as diclofenac. Further examples of NSAIAs are listed below:

| | | |
|---|---|---|
| loxoprofen | tolfenamic acid | indoprofen |
| pirprofen | clidanac | fenoprofen |
| naproxen | fenclorac | meclofenamate |
| benoxaprofen | carprofen | isofezolac |
| aceloferac | fenbufen | etodolic acid |
| fleclozic acid | amfenac | efenamic acid |
| bromfenac | ketoprofen | fenclofenac |
| alcofenac | orpanoxin | zomopirac |
| diflunisal | pranoprofen | zaltoprofen |

The preferred compounds are those wherein "A" is selected from the ester or amide derivatives of naproxen, flurbiprofen or diclofenac. The most preferred compounds are those wherein "A" is selected from the ester or amide derivatives of naproxen or flurbiprofen.

With respect to the other substituents of the compounds of formula (I), the preferred compounds are those wherein:

X is O or NR;

R is H or $C_1$–$C_3$ alkyl;

Y is CH(OH), and m is 0 to 2 and n is 1 or 2, or Y is not present, and m is 1 or 2 and n is 0 to 4;

Z is a, b, d or e;

R' and $R^3$ are H or $C(O)CH_3$; and

R" is $CH_3$.

The most preferred compounds are those wherein:

X is O or NR;

R is H;

Y is CH(OH) or is not present;

m is 0 or 1;

n is 1;

Z is a, b, d or e;

R' and $R^3$ are H; and

R" is $CH_3$.

The following compounds are particularly preferred:

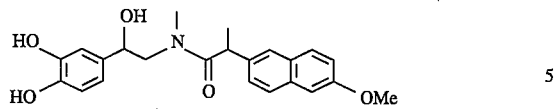

N-(2-(3,4-dihydroxyphenyl)-2-hydroxyethyl)-N-methyl 2-(6-methoxy-2-naphthyl)propionamide ("Compound A");

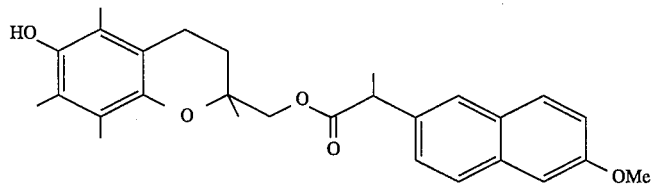

2-(6-hydroxy-2,5,7,8-tetramethyl-3,4-dihydro-2H-benzo[1,2-b]pyran-2-yl)methyl 2-(6-methoxy-2-naphthyl)propionate ("Compound B");

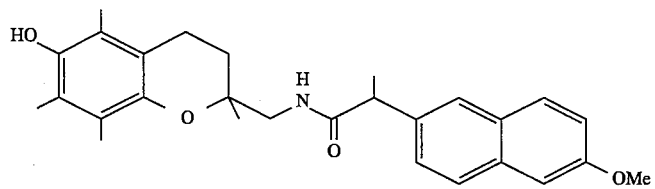

N-(2-(6-hydroxy-2,5,7,8-tetramethyl-3,4-dihydro-2H-benzo[1,2-b]pyran-2-yl)methyl) 2-(6-methoxy-2-naphthyl)propionamide ("Compound C");

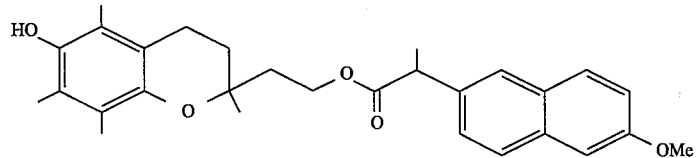

2-(6-hydroxy-2,5,7,8-tetramethyl-3,4-dihydro-2H-benzo[1,2-b]pyran-2-yl)ethyl 2-(6-methoxy-2-naphthyl)propionate ("Compound D");

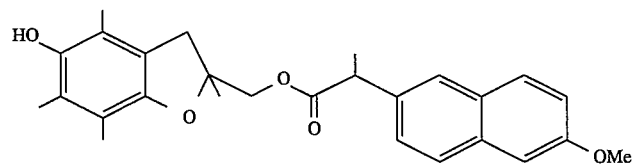

2-(5-hydroxy-2,4,6,7-tetramethyl-2,3-dihydro-benzo[1,2-b]furan-2-yl)methyl 2-(6-methoxy-2-naphthyl)propionate ("Compound E");

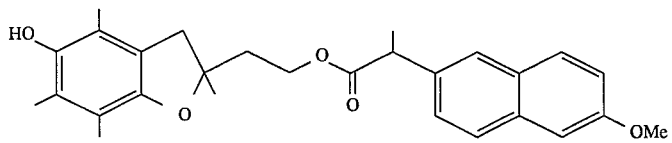

2-(5-hydroxy-2,4,6,7-tetramethyl-2,3-dihydro-benzo[1,2-b]furan-2-yl)ethyl 2-(6-methoxy-2-naphthyl)propionate ("Compound F"); and

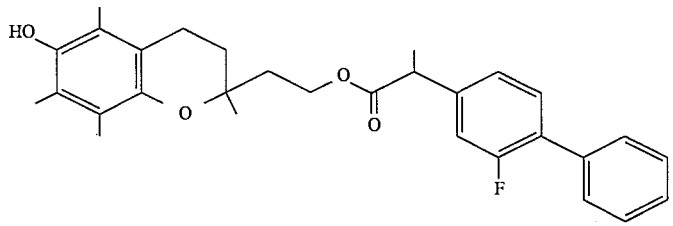

2-(6-hydroxy-2,5,7,8-tetramethyl-2,3-dihydro-2H-benzo[1,2-b]pyran-2-yl)ethyl 2-(3-fluoro-4-phenyl-phenyl)propionate ("Compound G").

The compounds of the present invention may be prepared by the methods illustrated in Scheme 1 below:

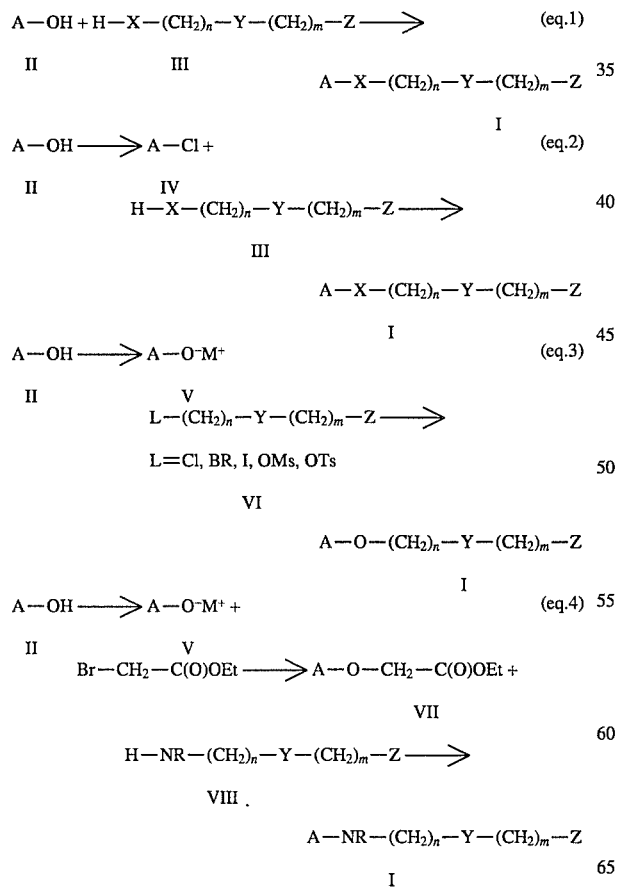

The conversion of the carboxylic acid containing nonsteroidal anti-inflammatory agents (II) to esters or amides (I) may be carried out by the following methods:

(i) As illustrated in equation 1 above, carboxylic acids (II) may be reacted with the appropriate amine or alcohol derivative (III) in the presence of a coupling reagent, such as dicyclohexylcarbodiimide or 1-(3-dimethylaminopropyl)3-ethyl carbodiimide HCl, and 4-dimethylamine pyridine or 1-hydroxybenzotriazole, in an inert organic solvent, such as acetonitrile or tetrahydrofuran, and at a temperature from 0° C. to 50° C.

(ii) As illustrated in equation 2 above, carboxylic acids (II) may be converted to acid chlorides (IV) by reacting them with a reagent such as thionyl chloride or oxalyl chloride, in the presence of an inert solid or neat, at a temperature from 0° C. to 80° C. The resulting acid chloride (IV) may be reacted with the desired amine or alcohol (III) in an inert solvent such as tetrahydrofuran, in the presence of pyridine or a tertiary amine, such as triethylamine.

(iii) As illustrated in equation 3 above, esters (I) may be formed by reacting carboxylate anions (V), formed by reacting the carboxylic acid (II) with a base such as sodium hydride, with a halide (iodide, bromide, chloride) or sulfonate (mesylate, tosylate) (VI), in a solvent such as acetonitrile or dimethylformamide, at a temperature from 0° C. to 100° C.

(iv) As illustrated in equation 4 above, amides (I) may be prepared by reacting carboxylate anions (V), formed by reacting carboxylic acid (II) with a base such as sodium hydride, with ethyl bromoacetate. The resulting ester (VII) is reacted with the desired amine (VIII), neat or in an inert solvent, such as acetonitrile or dimethylformamide, at a temperature from 0° C. to 100° C.

The intermediate compounds (X) of Scheme 2 below, which can be used as compounds (III) and (VIII), were prepared using the general methods described in *Journal of Organic Chemistry*, volume 54, pages 3282–3292, (1989). The nitrile (IX) can be reduced using a reagent such as lithium aluminum hydride to afford the amine (X), which may be isolated as the hydrochloride salt.

The use of certain protecting groups and deprotection steps may be necessary, as will be appreciated by those skilled in the art.

Scheme 2

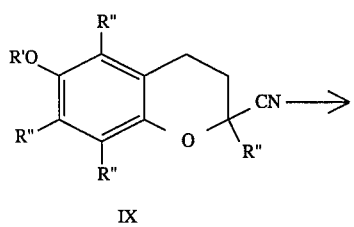

IX

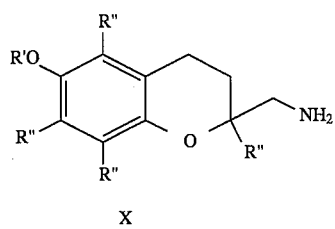

X

Compounds of formula (I) may exist as mixtures of stereoisomers. The preparation of the individual stereoisomers may be effected by preparing and resolving the acids (II), by known methods, and then using a single stereoisomer as starting material. Compounds (III), (VI) and (VIII) may be prepared as single stereoisomers from compounds of formula ($XI_{a-d}$), shown in Table 1 below, using known methods:

TABLE 1

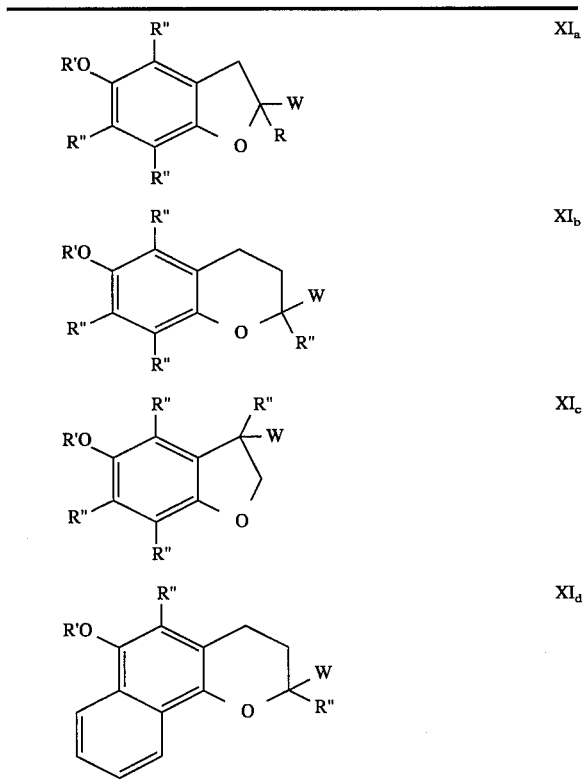

wherein:

W is $(CH_2)_p$-Q;

p is 0–1;

Q is $CH_2OH$ or $CO_2H$;

R' is H, C(O)R, C(O)$NR_2$, $PO_3^-$, or $SO_3^-$; and

R" is H or $C_1$–$C_6$ alkyl.

The alcohols ($XI_{a-d}$) may be resolved by forming esters with optically active carboxylic acids, separating the diastereomers, and then hydrolyzing the resolved diastereomers. The corresponding carboxylic acids ($XI_{a-d}$) may be resolved by forming an ester with an optically active alcohol, separating the diastereomers, and then hydrolyzing the resolved diastereomers. Or, the carboxylic acids ($XI_{a-d}$) may be resolved by forming an amine salt with an optically active amine. Separation by recrystallization and neutralization of the resolved carboxylic acid salt may be utilized to provide the resolved carboxylic acid. Resolution of the esters and amides (I) may also be effected using chromatographic techniques known to those skilled in the art.

The amines of formula (I), where Y is NR, may be converted to amine salts by reacting the amine with acids of sufficient strength to produce an organic or inorganic salt. The pharmaceutically acceptable anions include: acetate, bromide, chloride, citrate, maleate, fumarate, mesylate, phosphate, sulfate and tartrate.

Methods of synthesizing the compounds formula (I) are further illustrated by the following examples:

EXAMPLE 1

Synthesis of
N-(2(3,4,dihydroxyphenyl)-2,hydroxyethyl)-N-methyl
2-(6-methoxy-2-naphthyl)propionamide Epinephrine (Aldrich, 3.18 grams [g], 17.3 millimoles [mmol]), 1-hydroxylbenzotriazole hydrate (Aldrich, 1.76 g, 12.9 mmol) and 1-(3-dimethylaminopropyl)-3-ethyl carbodiimide HCl (Aldrich, 2.49 g, 12.9 mmol) were added to acetonitrile (200 milliliters [ml]). After stirring for 10 minutes, a solution of 6-methoxy-α-methyl-2-naphthaleneacetic acid (Aldrich, 2.0 g, 8.66 mmol), in 50 ml of acetonitrile, was added dropwise. After stirring for 16 hours, the reaction mixture was concentrated in vacuo (under reduced pressure), and the residue was partitioned between water (100 ml) and methylene chloride (100 ml). The layers were separated and the aqueous layer was extracted with methylene chloride (2× 50 ml) and ethyl acetate (50 ml). The combined organic extracts were treated with methanol until a clear solution was formed. This solution was dried (magnesium sulfate) and concentrated in vacuo. Flash chromatography of the residue (silica gel, 95:5, volume:volume [v:v], methylene chloride:methanol), and concentration of the appropriate fractions resulted in the formation of a solid. The solid was recrystallized from a mixture of ethyl acetate and hexane to give N-(2(3,4-dihydroxyphenyl)-2-hydroxyethyl)-N-methyl-2-(6-methoxy-2-naphthyl)propionamide, a mixture of diastereomers, as a white solid (0.95 g, 27% yield).

$^1$H NMR (CDCl$_3$) δ1.25–1.49 (m, 3H), 2.88 (d, 3H), 3.75–4.20 (m, 2H), 3.90 (s, 3H),4.80 (m, 1H), 6.5–7.8 (m, 12H).

Elemental Analysis: Calculated for $C_{23}H_{25}NO_5$●0.5 $H_2O$ Calculated for: C, 68.30; H, 6.48; N, 3.46. Found: C, 68.35; H, 6.49; H, 3.43. Melting point: 115°–117° C.

EXAMPLE 2

Synthesis of
2-(6-hydroxy-2,5,7,8-tetramethyl-3,4-dihydro-
2H-benzo[1,2-b]pyran-2-yl)methyl
2-(6-methoxy-2-naphthyl)propionate A solution of 6-hydroxy-2,5,7,8-tetramethyl-2H-1-benzo [1,2-b]pyran-2-yl)methanol (2.00 g, 8.46 mmol), 6-methoxy-α-methyl naphthaleneacetic acid (2.14 g, 9.31 mmol), dimethylaminopyridine (Aldrich, 1.24 g, 10.00 mmol) and 1-(3-dimethylamino propyl)-3-ethyl-carbodiimide hydrochloride (1.71 g, 8.89 mmol), in tetrahydrofuran (40 mL), was stirred at ambient temperature under nitrogen for 72 hours. The reaction mixture was then diluted with ethyl acetate (200 mL), washed with 0.5N hydrochloride (2×250 mL), followed by water (2×250 mL), and then dried (sodium sulfate) and concentrated in vacuo. Flash chromatography of the residue (silica gel, 100–50:0–50, v:v, hexanes:ethyl acetate), and concentration of the appropriate fractions provided an oil. Crystallization from ethyl acetate-hexanes gave 2.21 g (58.3% yield) of an impure white solid. The solid was then chromatographed, and the appropriate fractions were collected and concentrated. The solid that formed was recrystallized from a mixture of ethyl acetate and hexanes to give 0.80 g (21.1% yield) of a white solid.

$^1$H-NMR (CDCl$_3$) δ:1.15 (s, 3H), 1.57–1.61 (d, 3H), 1.62–1.88 (m, 2H), 1.98–2.11 (m, 9H), 2.40–2.59 (m, 2H), 3.82–3.92 (m, 1H), 3.91 (s, 3H), 4.01–4.22 (m, 3H), 7.09–7.16 (m, 2H), 7.34–7.41 (m, 1H), 7.55–7.68 (m, 2H).

Elemental Analysis: Calculated for $C_{28}H_{32}O_5$. Calculated: C, 74.98; H, 7.19. Found: C, 75.15, H, 7.08. Melting point: 103°–105° C.

EXAMPLE 3

Synthesis of
N-[(6-hydroxy-2,5,7,8-tetramethyl-3,4-dihydro-2H-1-benzo[1,2-b]pyran-2-yl)methyl]2-(6-methoxy-2-naphthyl)propionamide The intermediate, (6-hydroxy-2,5,7,8-tetramethyl-3,4-dihydro-2H-1-benzo[1,2-b]pyran-2-yl)methylamine, was first synthesized:

A 1 molar (M) ethereal solution of lithium aluminum hydride (Aldrich, 32.4 mL, 32.43 mmol) was added slowly over a 5 minute period to a chilled, (4°–6° C.) stirring solution of (2-cyano-6-hydroxy-2,5,7,8-tetramethyl-3,4-dihydro-2H-1-benzo[1,2-b]pyran in tetrahydrofuran (50 mL). After 2 hours, the reaction mixture was quenched by the slow sequential addition of 10% aqueous tetrahydrofuran (30 mL), 15% sodium hydroxide (10 mL) and then water (20 mL), while stirring. The resulting suspension was filtered through celite, and the celite pad was washed with ethyl ether (400 mL). The organic layer was separated, dried (Na$_2$SO$_4$), and concentrated in vacuo, resulting in a residue. A 1M ethereal solution of hydrochloride was then added to a solution of the residue in ethyl ether (100 mL), a solid formed, and the solid was then collected by filtration and washed with ethyl ether to give 2.31 g (65.4% yield) of a white solid. The product was used crude in the next reaction.

$^1$H-NMR (DMSO-d$_6$/TMS): 1.15 (s, 3H), 1.75 (t, 2H), 1.99 (s, 6H), 2.01 (s, 3H), 2.54 (t, 2H), 2.98 (s, 2H). MS (CI): 236 (m+1).

The hydrochloride salt of (6-hydroxy-2,5,7,8-tetramethyl-3,4-dihydro-2H-1-benzo[1,2-b]pyran-2-yl)methylamine (0.30 g, 1.10 mmole) and 6-methoxy-α-methyl naphthaleneacetic acid (Aldrich, 0.28 g, 1.21 mmole) were stirred in the presence of dimethylaminopyridine (Aldrich, 0.26 g, 2.20 mmole) and 1-(3-dimethylaminopropyl)-3-ethylcarbodiimide hydrochloride (Janssen Chimica-Spectrum, 0.21 g, 1.10 mmole), in tetrahydrofuran (4.0 mL) under an atmosphere of nitrogen. After stirring 17 hours at ambient temperature, the reaction mixture was diluted with ethyl acetate (70 mL), washed with water (2×15 mL), followed by brine (15 mL) and then dried (sodium sulfate). The mixture was concentrated in vacuo and the residue subjected to flash chromatography (silica gel, 100–50:0–50, v:v, hexanes:ethyl acetate). The appropriate fractions were concentrated in vacuo, and the resulting crystalline foam suspension was then washed in hexanes to give 0.28 g (58.3% yield) of N-[(5-hydroxy-2,5,7,8-tetramethyl-3,4-dihydro-2H-1-benzopyran-2-yl)methyl]-2-(6-methoxy-2-naphthyl)propionamide as a white amorphous solid.

$^1$H-NMR (CDCl$_3$) d 1.03–1.08 (d,3H), 1.57–1.64 (m, 6H), 1.70 (t, 2H,), 2.04–2.05 (m, 6H,), 2.48–2.51 (m, 2H), 3.16–3.58 (m, 2H), 3.74 (q, 1H), 3.91 (s, 3H), 4.91 (br s, 1H) 5.751 (t, 1H), 7.01–7.19 (m, 2H), 7.29–7.40 (t, 1H), 7.52–7.81 (m, 3H).

Elemental Analysis: Calculated for $C_{28}H_{33}NO_4$ Calculated: C, 75.14; H, 7.43; N, 3.13. Found: C, 75.04; H, 7.50; N, 2.97. Melting point: 67°–70° C.

EXAMPLE 4

Synthesis of
2-(6-hydroxy-2,5,7,8-tetramethyl-3,4-dihydro-2H-benzo[1,2-b]pyran-2yl)ethyl
2-(6-methoxy-2-naphthyl)propionate A solution of 1,3-dicyclohexylcarbodiimide (Aldrich, 0.89 g, 4.31 mmol) in acetonitrile (25 mL), was added dropwise to a stirring slurry of (+)-6-methoxy-α-methyl-2-naphthaleneacetic acid (Aldrich, 0.90 g, 3.91 mmol), 2-hydroxy-2,5,7,8-tetramethyl-3,4-dihydro-2H-benzo[1,2-b]pyran-2yl)ethanol (0.98 g, 3.91 mmol, U.S. Pat. No. 5,266,709 column 45) and 1-hydroxybenzotriazole hydrate (Aldrich, 0.59 g, 4.31 mmol), in acetonitrile (50 mL). After stirring for 18 hours, the reaction mixture was concentrated in vacuo. The residue was partitioned between water (30 mL) and methylene chloride (30 mL). The layers were separated, and the aqueous layer was extracted with methylene chloride (2×20 mL). The combined organic extracts were washed with water (20 mL), then dried (magnesium sulfate) and concentrated in vacuo. Flash chromatography (silica gel, 2:8, v:v, ethyl acetate:hexanes) of the residue afforded a white solid upon the concentration of the appropriate fractions. The white solid was recrystallized from an ethyl acetate-hexanes mixture to give 0.60 g (33.1% yield) of 2-(6-hydroxy-2,5,7,8-tetramethyl-3,4-dihydro-2H-benzo[1, 2-b]pyran-2yl)ethyl 2-(6-methoxy-2-naphthyl)propionate, a mixture of diastereomers, as a white solid.

$^1$H NMR (CDCl$_3$) δ1.1 (d, 3H), 1.6–1.5 (m, 3H), 1.6 (m, 2H), 1.9 (m,2H). 2.0 (s, 6H), 2.1 (s, 3H), 2.4 (t, 2H), 3.8 (q, 2H), 3.9 (s, 3H), 4.2 (s, 1H), 4.1–44 (m, 2H), 7.1–7.7 (m,6H).

Elemental Analysis: Calculated for $C_{29}H_{34}O_5$ Calculated: C, 75.30; H, 7.41. Found: C, 75.24; H, 7.46. Melting Point: 99.5°–101.5° C.

EXAMPLE 5

Synthesis of
2-(5-hydroxy-2,4,6,7-tetramethyl-3,4-dihydro-2H-benzol[1,2-b]furan-2-yl)methyl
2-(6-methoxy-2-naphthyl)propionate A solution of (5-hydroxy-2,4,6,7-tetramethyl-2,3-dihydrobenzo[1,2-b]furan-2-yl)methanol (0.78 g, 3.50 mmol) and 6-methoxy-α-methyl naphthaleneacetic acid (Aldrich, 0.89 g, 3.86 mmol) was stirred in the presence of dimethylaminopyridine (0.43 g, 3.51 mmol) and 1-(3-dimethylaminopropyl)-3-ethyl-carbodiimide hydrochloride (0.67 g, 3.51 mmol), in tetrahydrofuran (15 mL). The reaction mixture was stirred at ambient temperature under nitrogen for 24 hours, diluted with water (100 mL) and then washed with ethyl acetate (5×65 mL). The organic extracts were combined, and then dried (sodium sulfate) and concentrated in vacuo. The residue was subjected to flash chromatography (silica gel, 100–50:0–50, v:v, hexanes:ethyl acetate), and the appropriate fractions were combined to give 0.68 g (44.7% yield) of a foam residue. Crystallization from methylene chloridehexanes gave 0.24 g (15.8% yield) of a pale yellow solid.

$^1$H-NMR (CDCl$_3$): 1.33–1.35 (d, 3H), 1.51–1.55 (d, 3H), 1.92–1.94 (s, 3H), 2.00–2.03 (d, 3H), 2.09–2.11 (d, 3H), 2.56–2.57 (d, 1H), 2.58–2.91 (d, 1H,, 3.76–3.89 (m, 1H), 3.920 (s, 3H), 4.04–4.22 (m, 3H), 7.09–7.17 (m, 2H), 7.26–7.34 (m, 1H), 7.58–7.79 (m, 2H).

Elemental Analysis: Calculated for $C_{27}H_{30}O_5$. Calculated: C, 74.63; H, 6.96. Found: C, 74.42; H, 6.94. Melting point: 185.5°–187 ° C.

EXAMPLE 6

Synthesis of 2-(5-hydroxy-2,4,6,7-tetramethyl-3,4-dihydro-benzo[1,2-b]furan-2yl)ethyl 2-(6-methoxy-2-naphthyl)propionate A solution of 2-(5-hydroxy-2,4,6,7-tetramethyl-2,3-dihydrobenzo[1,2-b]furan-2-yl)ethanol (1.30 g, 5.51 mmol) and 6-methoxy-α-methyl naphthaleneacetic acid (Aldrich, 1.39 g, 6.06 mmol) was stirred in the presence of dimethylaminopyridine (0.67 g, 5.51 mmol) and 1-(3-dimethylaminopropyl)-3-ethyl-carbodiimide hydrochloride (1.06 g, 5.51 mmol), in tetrahydrofuran (25 mL). The reaction mixture was stirred at ambient temperature under nitrogen for 24 hours, diluted with ethyl acetate (150 mL), washed with water (2×40 mL) and then brine (30 mL). The organic extract was dried (sodium sulfate) and concentrated in vacuo. The residue was subjected to flash chromatography (silica gel, 100–50:0–50, v:v, hexanes:ethyl acetate), and the appropriate fractions were combined to give 1.84 g (74.5% yield) of a foam residue. Fractional crystallization and recrystallization from methylene chloride-hexanes gave 0.40 g (13.0% yield) of white solid.

$^1$H-NMR (CDCl$_3$): 1.34 (s, 3H), 1.54–1.57 (d, 3), 1.99 (t, 2H), 2.01 (s, 3H), 2.05 (s, 3H), 2.10 (s, 3), 2.73–2.81 (d, 1), 2.90–2.97 (d, 1), 3.77–3.89 (q, 1H), 3.91 (s, 3H), 4.102 (s, 1H, 4.165–4.29 (m, 2H), 7.10–7.16 (m, 2H), 7.35–7.40 (m, 1H), 7.64–7.70 (m, 2H).

Elemental Analysis: Calculated for $C_{28}H_{32}O_5$ 0.1 mole $CH_2Cl_2$. Calculated: C, 73.84; H, 7.10. Found: C, 73.85, 73.83; H, 7.12. Melting point: 129.5°–131° C.

EXAMPLE 7

Synthesis of 2-(6-hydroxy-2,5,7,8-tetramethyl-3,4-dihydro-2H-benzo[1,2-b]pyran-2yl)ethyl 2-(3-fluoro-4-phenyl-phenyl)propionate The intermediate, 2-(6-benzyloxy-2,5,7,8-tetramethyl-3,4-dihydro-2H-benzo[1,2-b]pyran-2yl)ethyl 2-(3-fluoro-4-phenyl-phenyl)propionate, was first synthesized:

A solution of flubiprofen (Sigma, 2.0 g, 8.2 mmol), 2-(6-benzyloxy-2,5,7,8-tetramethyl-3,4-dihydro-2H-benzo[1,2-b]pyran-2yl)ethanol (2.4 g, 8.2 mmol) 1-hydroxybenzotriazole hydrate (Aldrich, 2.4 g, 13.9 mmol) and 1-(3-dimethylaminopropyl)-3-ethyl-carbodiimide hydrochloride (Aldrich, 2.8 g, 12.3 mmol), in acetonitrile (40 ml), was stirred at ambient temperature. After 72 hours, the reaction mixture was concentrated in. vacuo and the residue partitioned between water and methylene chloride. A solid formed which was removed by filtration and discarded. The layers were separated and the aqueous layer was extracted with methylene chloride (2×25 ml). The combined organic extracts were then dried (magnesium sulfate) and concentrated in vacuo. The residue was chromatographed (silica gel, 2:8, v:v, ethyl acetate:hexane). Concentration of the appropriate fractions afforded 3.0 g (64% yield, mixture of stereoisomers) of the product as a clear oil.

$^1$H NMR (CDCl$_3$) δ: 1.23–1.27 (m, 3H), 1.53–1.57 (m, 3H), 1.75 (m, 2H), 1.95 (m, 2H), 2.08 (s, 3H), 2.14 (s, 3H), 2.21 (s, 3H), 2.55 (t, 3H), 3.75 (m, 2H), 4.3 (m, 1H), 4.65 (s, 2H), 7.1–7.7 (m, 13H).

A solution of 2-(6-benzyloxy-2,5,7,8-tetramethyl-3,4-dihydro-2H-benzo[1,2-b]pyran-2yl)ethyl 2-(3-fluoro4-phenyl-phenyl)propionate in ethyl acetate was treated with 10% palladium on charcoal (Aldrich, 0.5 g). The resulting mixture was hydrogenated on a Parr Apparatus [initial pressure 60 pounds/inch$^2$ (psi)]. After 18 hours, the reaction mixture was filtered, and the resulting solution concentrated in vacuo. The residue was subjected to flash chromatography (silica gel, 2:8, v:v, ethyl acetate:hexane). Concentration of the appropriate fractions afforded a clear oil. Hexane was added to the oil and a white solid formed upon standing. The white solid was collected by filtration to afford 0.91 g (36% yield) of 2-(6-hydroxy-2,5,7,8-tetramethyl-3,4-dihydro-2H-benzo[1,2-b]pyran-2yl)ethyl 2-(3-fluoro4-phenyl-phenyl)propionate as a mixture of stereoisomers.

$^1$H NMR (CDCl$_3$) δ: 1.22–1.23 (m, 3H), 1.51–1.55 (m, 3H), 1.65–1.8 (m, 2H), 1.85–2.00 (m, 2H), 2.08 (s, 6H), 2.14 (s, 3H), 2.57 (t, 2H), 3.75 (q, 1H), 4.1–4.5 (m, 2H), 7.10–7.65 (m, 8H).

Elemental Analysis: Calculated for $C_{30}H_{33}OF_4$. Calculated: C,75.60; H, 6.98. Found: C,75.69; H,7.01. Melting point: 85°–87° C.

The compounds of formula (I) may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. The ophthalmic compositions of the present invention will include one or more compounds of formula (I) and a pharmaceutically acceptable vehicle for said compound(s). Various types of vehicles may be utilized. The vehicles will generally be aqueous in nature. Aqueous solutions are generally preferred, based on ease of formulation, as well as patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for compounds of formula (I) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium 1, or other agents known to those skilled in the art. Such preservatives are typically employed at a level of from 0.001 to 1.0 percent by weight, based on the total weight of the composition (wt. %).

Some of the compounds of formula (I) may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., U.S.A.); cyclodextrin; or other agents known to those skilled in the art. Such co-solvents are typically employed at a level of from 0.01 to 2 wt. %.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 wt. %.

The pharmaceutical compositions containing one or more compounds of formula (I) may be used to treat patients afflicted with or prone to various types of cellular damage. In particular, these compositions may be used for inflammation and allergic diseases where prostaglandins and leukotrienes are known to participate. The concentrations of the compounds in the compositions will depend on various factors, including the nature of the condition to be treated with the compositions. However, the compositions will generally contain one or more of the compounds in a concentration of from about 0.001 to about 5 wt. %.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formula (I) to prevent or reduce damage to ophthalmic tissues at the cellular level is a particularly important aspect of the present invention. Ophthalmic conditions which may be treated include, but are not limited to, cataracts, retinopathies, heredodegenerative diseases, macular degeneration, ocular ischemia, neovascular diseases, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments. The compounds may also be used as an adjunct to ophthalmic surgery, such as by vitreal or subconjunctival injection following ophthalmic surgery.

The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formula (I) is preferred when the compounds are administered intraocularly. As utilized herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., U.S.A.) are examples of physiologically balanced intraocular irrigating solutions. The latter type of solution is described in U.S. Pat. No. 4,550,022 (Garabedian, et al.), the entire contents of which are hereby incorporated in the present specification by reference.

The doses utilized for any of the above-described purposes will generally be from about 0.01 to about 100 milligrams per kilogram of body weight (mg/kg), administered one to four times per day.

The compounds of the present invention are further illustrated by the following in vitro and in vivo biological activity examples.

EXAMPLE 8

The antioxidant activity of representative compounds of the present invention, as compared with Vitamin E, is presented in Table 2 below. Antioxidant activity was measured using a phospholipid oxidation assay. Liposomes were formed from dilineoleolylphosphocholine and the test compound. Free radical damage was induced by exposure to $Fe^{+3}$/EDTA (167 micromolar [$\mu M$]) and ascorbate (167 $\mu M$). Oxidation was terminated after one hour by freezing in liquid nitrogen. Lyophilized samples were then dissolved in methanol or water. Oxidation was measured by conjugate diene formation, monitored using UV spectroscopy as described in *Biochimica et Biophyica Acta*, volume 1081, 181–187, (1991). The $IC_{50}$ was calculated using the following non-linear regression algorithm: $Y=A/[1+(B/X)^c]$, wherein A=maximum, B=$IC^{50}$ and c=cooperativity or relative broadness of the curves. The minimum was assumed to be zero.

TABLE 2

| Compound | Phospholipid Oxidation $IC_{50}$ ($\mu M$) |
| --- | --- |
| Compound B | 1.16 |
| Compound D | 2.23 |
| Compound E | 2.48 |
| Compound F | 2.55 |
| Vitamin E | 4.42 |

Inhibition of lipid peroxide formation by representative compounds of the present invention, as compared with Vitamin E, is shown in Table 3 below. The cytoprotective effects of the compounds were measured using bovine retinal pieces. Retinal tissues were incubated in hypoxic media for 1 hour. After 50 minutes of hypoxia, test agents were added to the media to allow 10 minutes for the drug to diffuse into the tissue prior to reoxygenation. The vehicle by itself, was added to the non-drug group. Following the incubation period, tissue was reoxygenated for 1 hour. Lipid peroxidation was assessed by the formation of thiobarbituric acid reacting substances (TBARS). The tissues were homogenized and added to the trichloroacetic acid-thiobarbituric acid reagent and heated in the presence of BHT. The homogenate was filtered and the absorbance of the supernant was measured spectrophotometrically. A double derivative technique was used to calculate the concentration of TBARS present in each sample. Quantitation was based on a molar extinction coefficient of $1.56 \times 10^5$.

TABLE 3

| Compound | Retinal Pieces $IC_{50}$ (μM) |
| --- | --- |
| Compound A | 0.15 |
| Compound D | 0.006 |
| Compound E | 0.01 |
| Vitamin E | 5.0 |

EXAMPLE 10

5-lipoxygenase inhibition by representative compounds of the present invention is shown in Table 4 below. The 5-lipoxygenase inhibitor activity was determined by measuring the inhibition of 5-HETE and $LTB_4$ formation. The ability of a compound to suppress 5-HETE and $LTB_4$ formation was investigated in calcium ionophore ($A_{23187}$)-stimulated neutrophils isolated from rabbit peripheral blood. Neutrophils were isolated by standard procedures. Briefly, heparinized/calcium chelated blood was obtained from New Zealand Albino (NZA) rabbits by heart puncture. Red cells were removed at 4° C. by dextran sedimentation, as described in *Blood*, volume 11, 436 (1956). White cells, contained in the supernatant fraction, were sedimented by centrifugation and contaminating red cells removed by hypotonic lysis. The white cell pellet obtained, following red cell lysis and centrifugation, was resuspended in Dulbecco's PBS ($Ca^{2+}/Mg^{2+}$-free) and layered onto a 60% Histopaque-1083®/40% Histopaque-1119® cushion (Sigma Chemical, St. Louis, Mo., U.S.A.). The Histopaque® cushion was then centrifuged, and the resulting neutrophil pellet was washed and resuspended in 1/25 of the original blood volume. Aliquots of the cell suspension were pretreated for 5 minutes at 37° C. with carrier (DMSO) or test article dissolved in DMSO. $CaCl_2$ was immediately added to the cell suspension and cells stimulated by addition of 5 microliters [μl] of a mixture containing [1-$^{14}$C]-arachidonic acid and A23187 in DMSO. Final concentrations of $CaCl_2$, [1-$^{14}$C]-arachidonic acid and A23187 were 5.0 millimolar [mM], 52 μM and 5.0 μM, respectively. After 3 minutes of incubation at 37° C., reactions were terminated by addition of 2 volumes of acetone. Extraction and reversed phase ($C_{18}$-5 μ) HPLC analysis of [1-$^{14}$C]-labeled arachidonic acid metabolites are conducted as described by Graff and Anderson in *Prostaglandins*, volume 38, 473 (1989).

TABLE 4

| Compound | 5-Lipoxygenase Inhibition $IC_{50}$ (μM) |
| --- | --- |
| Compound A | 4.0 |
| Compound D | 1.0 |

EXAMPLE 11

The topical ophthalmic activity of representative compounds of the present invention, as compared with dexamethasone, is shown in Table 5 below. The compounds were evaluated in an endotoxin-induced uveitis model. This subacute model of ocular inflammation is characterized by the infiltration of neutrophils into the ocular tissue following administration of an endotoxin.

Ocular inflammation in female Lewis rats was initiated by hindpaw injection of 0.1 milliliters [ml] sterile saline (0.9% NaCl, weight:volume [w:v]) containing 200 milligrams [mg] bacterial endotoxin (LPS; *Escherichia coli* 055:B5). Test compound or vehicle (carbopol/maxidex), 5 μl, was administered topically to each eye of the experimental animal 20 and 24 hours prior to endotoxin injection, immediately before endotoxin injection, and 4 and 20 hours after endotoxin injection. Twenty-four hours post endotoxin injection, animals were sacrificed by $CO_2$ inhalation, and total ocular polymorphonuclear neutrophil (PMN) content was assessed indirectly by determination of myleoperoxide activity (MPO).

Ocular tissues were prepared for the quantification of neutrophil content as follows: Eyes were homogenized in 2.5 ml of ice-cold 50 mM phosphate/10 mM N-ethylmaleimide buffer. The Brinkman homogenation probe was rinsed three (3) times with 2.5 ml of the same buffer and the probe washings were combined with the initial tissue homogenate. The homogenate was centrifuged for 30 minutes at 12,000× gravitational constant [g] at 4° C. The supernatant was discarded and the proteinaceous pellet was solubilized on 0.5 ml of ice-cold 0.5% hexadecyltrimethyl ammonium bromide (HTABr)/50 mM phosphate buffer (pH 6.0). The detergent-treated pellet homogenate was centrifuged at 4° C. for 30 minutes at 12,000×g and the supernatant collected and assayed for MPO activity in a buffer containing 50 mM phosphate/250 mM HTABr/250 μM hydrogen peroxide and 1.5 mM o-dianisidine (pH 6.0). o-Dianisidine oxidation was monitored spectrophotometrically at a wavelength of 460 nanometers [nm].

TABLE 5

| Compound | Concentration (%) | % Inhibition of Influx |
| --- | --- | --- |
| Compound A | 0.1 | 40 |
| Compound D | 1.0 | 40 |
| Dexamethasone | 0.1 | 93 |

As shown in Table 5 above, Compounds A and D significantly inhibited neutrophil influx into the rat eye in the endotoxin induced uveitis model of ocular inflammation following topical administration.

What is claimed:
1. A compound of formula:

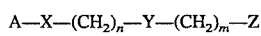

wherein:
A is a non-steroidal anti-inflammatory agent originally having a carboxylic acid moiety selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceclofenac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac;

X is O or NR;

A—X is an ester or amide linkage derived from the carboxylic acid moiety of the non-steroidal anti-inflammagtory, agent and the X;

R is H, $C_1$-$C_6$ alkyl or $C_3$-$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is selected frown the group consisting of:

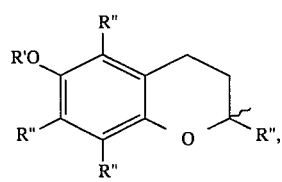 a

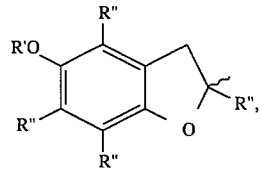 b

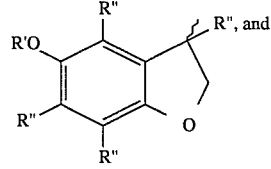 c

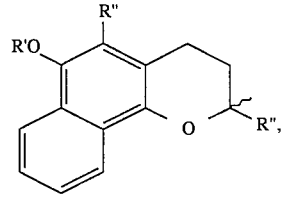 d wherein:
R' is H, C(O)R, $C(O)N(R)_2$, $PO_3^-$ or $SO_3^-$;

R" is H or $C_1$-$C_6$ alkyl;

or a pharmaceutically acceptable salt thereof.

2. A compound according to claim 1, wherein:
R is H or $C_1$-$C_3$ alkyl;
Y is CH(OH), m is 0 to 2, and n is 1 or 2, or Y is not present, m is 1 or 2, and n is 0 to 4;
Z is a, b or d;
R' is H, C(O)CH$_3$; and
R" is CH$_3$.

3. The compound according to claim 1, wherein the non-steroidal anti-flammatory agent is selected from the group consisting of:
fenamic acids; and indoles.

4. A compound according to claim 3, wherein:
R is H or $C_1$-$C_3$ alkyl;
Y is CH(OH), m is 0 to 2, and n is 1 or 2, or Y is not present, m is 1 or 2, and n is 0 to 4;
Z is a, b or d;
R' is H, C(O)CH$_3$; and
R" is CH$_3$.

5. A compound according to claim 1, wherein the non-steroidal anti-inflammatory agent is selected from the group consisting of naproxen, flurbiprofen and diclofenac.

6. A compound according to claim 5, wherein A is naproxen.

7. A compound according to claim 5, wherein A is flurbiprofen.

8. A compound according to claim 5, wherein A is diclofenac.

9. A compound according to claim 5, wherein:
R is H or $C_1$-$C_3$ alkyl;
Y is CH(OH), wherein m is 0 to 2 and n is 1 or 2, or Y is not present, wherein
m is 1 or 2 and n is 0 to 4;
Z is a, b or d;
R' is H, C(O)CH$_3$; and
R" is CH$_3$.

10. A compound according to claim 9, wherein A is naproxen.

11. A compound according to claim 9, wherein A is flurbiprofen.

12. A compound according to claim 9, wherein A is diclofenac.

13. A compound according to claim 1, wherein the compound has the following formula:

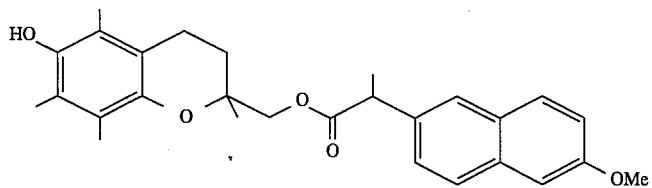

14. A compound according to claim 1, wherein the compound has the following formula:

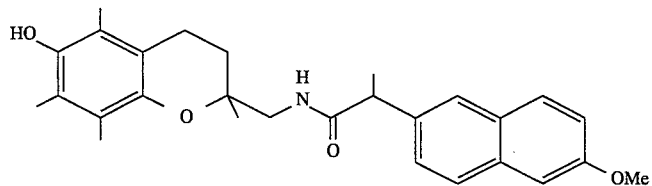

15. A compound according to claim 1, wherein the compound has the following formula:

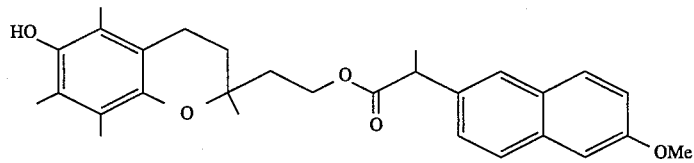

16. A compound according to claim 1, wherein the compound has the following formula:

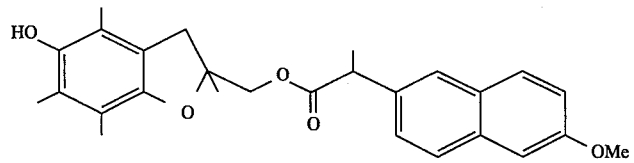

17. A compound according to claim 1, wherein the compound has the following formula:

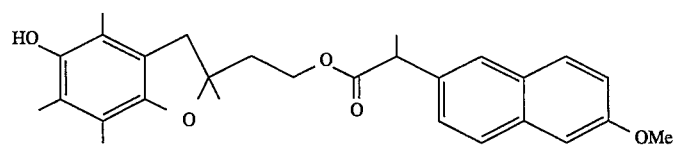

18. A compound according to claim 1, wherein the compound has the following formula:

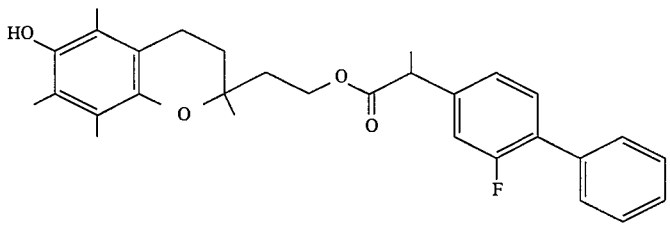

19. A pharmaceutical composition for preventing or alleviating damage to mammalian tissues comprising an amount of a compound of the following formula effective to decrease inflammation and free radical or oxidative damage in said tissues:

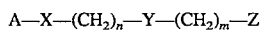

wherein:
A is a non-steroidal anti-inflammatory agent originally having a carboxylic acid moiety;
X is O or NR;
A—X is an ester or amide linkage derived from the carboxylic acid moiety of the non-steroidal anti-inflammatory agent and the X;
R is H, $C_1$-$C_6$ alkyl or $C_3$-$C_6$ cycloalkyl;
Y, if present, is O, NR, $C(R)_2$, CH(OH) or $S(O)_{n'}$;
n is 2 to 4 and m is 1 to 4 when Y is O, NR, or $S(O)_{n'}$;
n is 0 to 4 and m is 0 to 4 when Y is $C(R)_2$ or is not present;
n is 1 to 4 and m is 0 to 4 when Y is CH(OH);
n' is 0 to 2; and
Z is selected from the group consisting of:

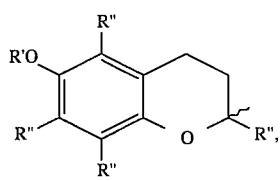 a

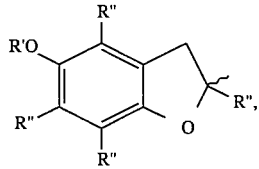 b

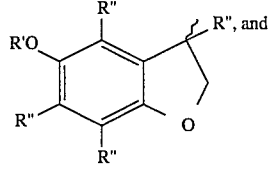 c

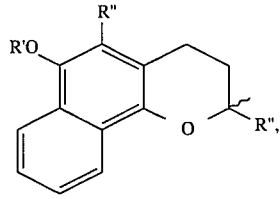 d wherein:
R' is H, C(O)R, $C(O)N(R)_2$, $PO_3^-$ or $SO_3^-$;

R" is H or $C_1$-$C_6$ alkyl;

or a pharmaceutically acceptable salt thereof; and a pharmaceutically acceptable vehicle therefore.

20. A composition according to claim 19, wherein:
R is H or $C_1$-$C_3$ alkyl;
Y is CH(OH), m is 0 to 2, and n is 1 or 2, or Y is not present, m is 1 or 2, and n is 0 to 4;
Z is a, b or d;
R' is H, $C(O)CH_3$; and
R" is $CH_3$.

21. The composition according to claim 19, wherein the non-steroidal anti-inflammatory agent is selected from the group consisting of: fenamic acids; indoles; and phenylalkanoic acids.

22. A composition according to claim 19, wherein the non-steroidal anti-inflammatory agent is selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceclofenac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

23. A composition according to claim 19, wherein the non-steroidal anti-inflammatory agent is selected from the group consisting of naproxen, flurbiprofen and diclofenac.

24. A composition according to claim 19, wherein the vehicle is a physiologically balanced irrigating solution.

25. A composition according to claim 19, wherein the compound is selected from the group consisting of:

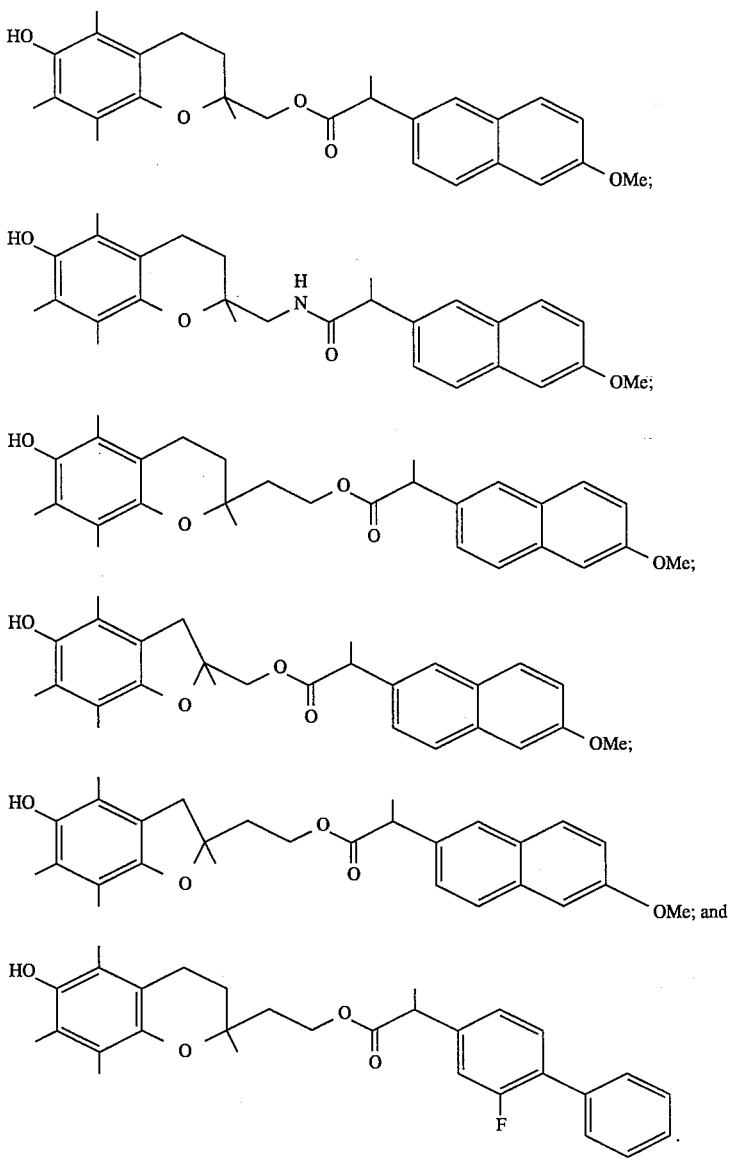

26. A method of preventing or alleviating damage to mammalian tissues which comprises administering a therapeutically effective amount of a composition comprising an amount of a compound of the following formula effective to decrease inflammation and free radical or oxidative damage in said tissues:

wherein:
- A is a non-steroidal anti-inflammatory agent originally having a carboxylic acid moiety;
- X is O or NR;
- A—X is an ester or amide linkage derived from the carboxylic acid moiety of the non-steroidal anti-inflammatory agent and the X;
- R is H, $C_1$–$C_6$ alkyl or $C_3$–$C_6$ cycloalkyl;
- Y, if present, is O, NR, $C(R)_2$, CH(OH) or $S(O)_{n'}$;
- n is 2 to 4 and m is 1 to 4 when Y is O, NR, or $S(O)_{n'}$;
- n is 0 to 4 and m is 0 to 4 when Y is $C(R)_2$ or is not present;
- n is 1 to 4 and m is 0 to 4 when Y is CH(OH);
- n' is 0 to 2; and
- Z is selected from the group consisting of:

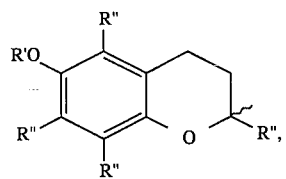

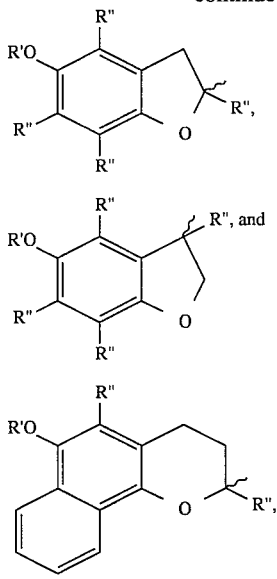

wherein:

R' is H, C(O)R, C(O)N(R)₂, PO⁻₃ or SO⁻₃;

R" is H or $C_1$–$C_6$ alkyl;

or a pharmaceutically acceptable salt thereof;

and a pharmaceutically acceptable vehicle thereof.

27. A method according to claim 26, wherein the composition is administered to prevent or alleviate damage to ophthalmic tissues.

28. A method according to claim 26, wherein:

R is H or $C_1$–$C_3$ alkyl;

Y is CH(OH), m is 0 to 2, and n is 1 or 2, or Y is not present, m is 1 or 2, and n is 0 to 4;

Z is a, b or d;

R' is H, C(O)CH₃; and

R" is CH₃.

29. The method according to claim 26, wherein the non-steroidal anti-inflammatory agent is selected from the group consisting of: fenamic acids; indoles; and phenylalkanoic acids.

30. A method according to claim 26, wherein the non-steroidal anti-inflammatory agent is selected from the group consisting of:

loxoprofen; tolfenamic acid; indoprofen; pirprofen; clidanac; fenoprofen; naproxen; fenclorac; meclofenamate; benoxaprofen; carprofen; isofezolac; acecloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

31. A method according to claim 26, wherein the non-steroidal anti-inflammatory agent is selected from the group consisting of naproxen, flurbiprofen and diclofenac.

32. A method according to claim 26, wherein the vehicle is a physiological balanced irrigating solution.

33. A composition according to claim 19, wherein the compound is selected from the group consisting of:

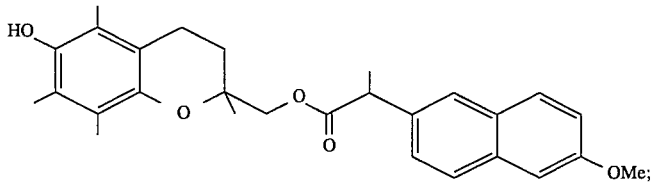

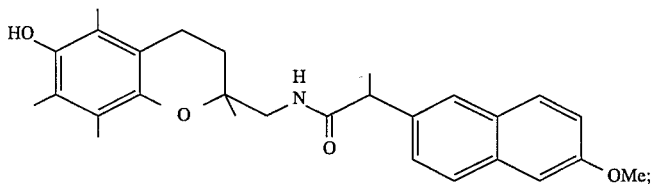

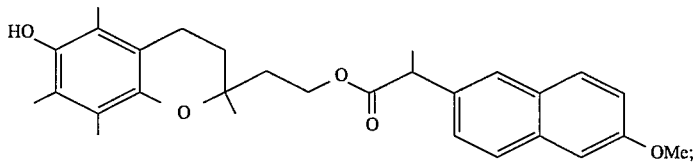

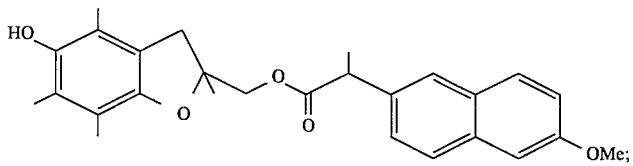

-continued
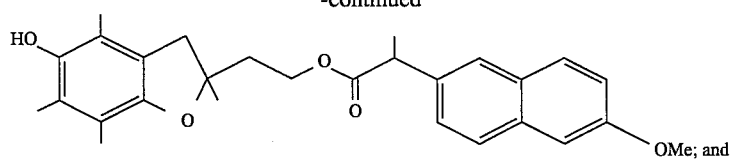
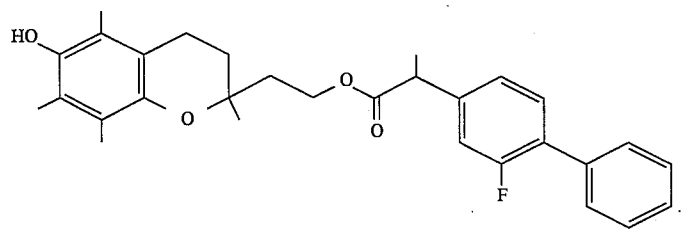
* * * * *